United States Patent [19]

Hodgkinson

[11] Patent Number: 5,500,485
[45] Date of Patent: Mar. 19, 1996

[54] MANUFACTURE OF N-PHOSPHONOMETHYLGLYCINE AND ITS SALTS

[76] Inventor: Ian Hodgkinson, 1 Bankfield Drive, Holmbridge, Huddersfield, Yorkshire HD7 1PH, United Kingdom

[21] Appl. No.: 261,792

[22] Filed: Jun. 20, 1994

[30] Foreign Application Priority Data

Jun. 21, 1993 [GB] United Kingdom ............ 9312740
Dec. 14, 1993 [GB] United Kingdom ............ 9325546

[51] Int. Cl.$^6$ ................................................ C07F 9/38
[52] U.S. Cl. ................................................ 562/18
[58] Field of Search ................................................ 562/18

[56] References Cited

U.S. PATENT DOCUMENTS

| | | | |
|---|---|---|---|
| 3,969,398 | 7/1976 | Hershman | 260/502.5 |
| 4,235,809 | 11/1980 | Redmore | 260/502.5 |
| 4,442,041 | 4/1984 | Subramanian | 260/502.5 F |
| 4,547,324 | 10/1985 | Wong | 260/502.4 R |
| 4,810,426 | 3/1989 | Fields, Jr. | 260/502.5 F |
| 4,853,159 | 8/1989 | Riley et al. | 562/17 |

FOREIGN PATENT DOCUMENTS 201957  5/1985  European Pat. Off. .

OTHER PUBLICATIONS

Vinke et al., *Heterogeneous Catalysis and Fine Chemicals II*, pp. 385–394, 1991, Amsterdam, Netherlands.
Van Dam et al., *Applied Catalysis*, 61 (1990) pp. 187–197.
Despeyroux et al., in New Developments in Scientific Oxidation (Centi, ed.), pp. 159 et seq. (1990).

*Primary Examiner*—José G. Dees
*Assistant Examiner*—Barbara S. Frazier

[57] ABSTRACT

N-Phosphonomethylglycine and its salts are manufactured by hydrolysing N-phosphonomethyl-2-oxazolidinone in an aqueous medium and thereafter oxidising the hydrolysis product in an aqueous alkaline medium using an oxygen-containing gas in the presence of an oxidation catalyst, for example a platinum or palladium catalyst optionally containing a promoter such as bismuth.

12 Claims, No Drawings

MANUFACTURE OF N-PHOSPHONOMETHYLGLYCINE AND ITS SALTS

This invention relates to the manufacture of N-phosphonomethylglycine and its salts and in particular to an improved process for the manufacture of N-phosphonomethylglycine and its salts from N-phosphonomethyl-2-oxazolidinone.

N-phosphonomethylglycine and its salts are well known compounds, active as herbicides. It is known to manufacture N-phosphonomethylglycine from N-phosphonomethyl-2-oxazolidinone, which is itself a convenient starting material and is readily prepared by the phosphonomethylation of 2-oxazolidinone as described for example U.S. Pat. No. 4,547,324.

U.S. Pat. No. 4,547,324 describes a process in which N-phosphonomethyl-2-oxazolidinone is reacted with an alkali or alkaline earth base in an aqueous solvent medium using cadmium oxide as catalyst followed by acidification resulting in the concurrent evolution of carbon dioxide and production of N-phosphonomethylglycine. The cadmium oxide is acting essentially as a de-hydrogenation catalyst and gaseous oxygen is not involved in the reaction. Cadmium oxide is said to be the only catalyst which is suitable for the oxidation stage. The reaction takes place at elevated pressure (about 500 psi to about 2000 psi) and at elevated temperature (about 220° C. to about 300° C.). Such elevated temperatures add considerably to the cost of a commercial plant operating the process and tend to favour the formation of unwanted by-products.

U.S. Pat. No. 4,810,426 proposes a variation on the process of U.S. Pat. No. 4,547,324. U.S. Pat. No. 4,810,426 discloses a process in which the hydrolysis of N-phosphonomethyl-2-oxazolidinone takes place under acid or neutral conditions such that the intermediate hydrolysis product, N-phosphonomethylethanolamine or the cyclic internal ester thereof, is completely formed before the aqueous medium is rendered alkaline and de-hydrogenation takes place in the presence of an oxide catalyst such as cadmium, zinc, copper, platinum and palladium oxides. As with the process of U.S. Pat. No. 4,547,324, gaseous oxygen is not involved in the reaction. It is said that the careful pH control of the two stage reaction is necessary to avoid the presence of alkali metal carbonate during the oxidation step which is stated to have an adverse effect on conversion. However, elevated temperature and pressure are still essential and the reaction forms a significant proportion of the undesired by-product aminomethylphosphonic acid.

We have now found that oxidation of the hydrolysis product of N-phosphonomethyl-2-oxazolidinone with an oxygen-containing gas in the presence of an oxidation catalyst provides a process which can be operated under relatively mild reaction conditions, thereby providing significant commercial advantages.

According to the present invention there is provided a process for the manufacture of N-phosphonomethylglycine and its salts which comprises hydrolysing N-phosphonomethyl-2-oxazolidinone in an aqueous medium and thereafter oxidising the hydrolysis product in an aqueous alkaline medium using an oxygen-containing gas in the presence of an oxidation catalyst.

The hydrolysis of N-phosphonomethyl-2-oxazolidinone may take place under alkaline or acidic conditions. In general however hydrolysis under acidic conditions requires relatively high temperatures and super-atmospheric, for example autogenous, pressure to be effective. This in turn places stringent requirements on the materials of construction of the plant and hydrolysis under the more mild alkaline conditions is thus preferred.

Thus hydrolysis under acidic conditions, for example in the presence of a mineral acid such as sulphuric acid, suitably takes place at a temperature of from 150° C. to 300° C. The reaction conveniently takes place in an autoclave under autogenous pressure.

The alkali used in the alkaline hydrolysis is suitably an alkali metal hydroxide or alkaline earth hydroxide, for example sodium hydroxide. The alkali used in the oxidation stage is suitably an alkali metal or alkaline earth metal hydroxide, for example sodium hydroxide. If desired, the intermediate formed by the hydrolysis of N-phosphonomethyl-2-oxazolidinone may be isolated prior to the oxidation stage but there is no particular necessity for isolation of the intermediate and in commercial practice, the hydrolysis intermediate will not generally be isolated. Thus it is preferred to use the same alkali to provide the alkaline medium for hydrolysis and the alkaline medium for oxidation, so that the two stages may be operated together and without isolation of the intermediate. If it is desired to adjust the concentration prior to the oxidation stage, a proportion of the water present may be removed, for example under vacuum. Preferably the alkali metal hydroxide used for both the hydrolysis and oxidation stages is sodium hydroxide.

It is believed that the product of the hydrolysis of N-phosphonomethyl-2-oxazolidinone is N-phosphonomethylethanolamine which will be in the form of the alkali salt when alkaline hydrolysis is used. However, the precise nature of the hydrolysis product is not material to the process of the present invention since it need never be isolated. Thus in contrast to the prior art process of U.S. Pat. No. 4,810,426, there is no requirement for a change in pH between the hydrolysis stage and the oxidation stage when the hydrolysis takes place under alkaline conditions. More specifically and as demonstrated hereafter in the Examples, we have found that the presence of sodium carbonate (derived from the reaction of the carbon dioxide hydrolysis product with the sodium hydroxide alkaline medium) has little or no adverse effect on the oxidation stage. Indeed, it is believed that any sodium carbonate present actually contributes to the necessary alkaline medium for the oxidation stage and may enable a corresponding reduction in the quantity of alkali required, for example a reduction in the quantity of sodium hydroxide required.

The hydrolysis of N-phosphonomethyl-2-oxazolidinone in the alkaline medium conveniently takes place at a temperature in the range from ambient to about 150° C., for example from about 50° C. to 130° C. Super-atmospheric pressure may be used if desired, for example autogenous pressure may be used at temperatures above the boiling point of the aqueous medium. In general however it is most convenient to undertake the alkaline hydrolysis reaction at reflux temperature of the reaction medium under atmospheric presure.

The oxygen-containing gas used in the oxidation stage is suitably oxygen itself or air. The oxygen-containing gas is suitably introduced into the reaction medium in a manner which maximises the contact therewith, for example by being sparged into the medium.

The oxidation catalyst may be any catalyst which is effective for oxygen gas/liquid phase catalysis, and suitably comprises a transition metal or precious metal oxidation catalyst, for example a platinum, palladium, ruthenium, copper, nickel, zinc, or iron catalyst. A mixed catalyst may be used, for example a mixed platinum/palladium catalyst. The oxidation catalyst may additionally comprise a promoter, for example bismuth, antimony, lead, tin or selenium, and in general we have found that such promoted catalysts show an improved catalyst life, for example if the catalyst is recovered and re-used for a number of reaction cycles. We have found that an especially effective catalyst system comprises platinum, or palladium or a mixture thereof in combination with a bismuth promoter, and in particular a palladium catalyst containing a minor proportion of platinum and bismuth as a promoter. Such catalyst systems may be prepared by known methods and are commercially available. The catalyst is preferably carried on a support such as a carbon support. Typical metal content for a palladium catalyst on the carbon support ranges for example from 2 to 8% by weight of palladium in combination with from 0 to 5% platinum and from 0 to 5% promoter, for example bismuth. Typical metal content for a platinum catalyst on the carbon support ranges for example from 2 to 8% by weight of platinum in combination with from 0 to 5% palladium and from 0 to 5% promoter, for example bismuth. The catalyst may be added to the reaction medium in finely divided form and subsequently recovered for re-use after reaction is complete. Alternatively the catalyst may form a stationary phase through which the reaction medium and oxygen-containing gas are passed.

The oxidation reaction may for example take place at atmospheric pressure and at a temperature in the range from ambient to 100° C., for example from 45° C. to 80° C. and there are obvious commercial advantages in being able to employ such relatively mild operating conditions. It will be appreciated however that operating at higher temperatures for example temperatures up to 150° C. and more particularly operating at super-atmospheric pressure, whilst increasing plant cost, may improve phase transfer between the aqueous and gaseous phases and hence may increase reaction rates. Those skilled in the art will be able to balance these factors in deciding an appropriate plant design.

Whilst the scope of the present invention is not to be considered as being limited by any one particular theory, it is believed that the mechanism of the oxidation stage of the present invention is very different from that of the de-hydrogenation stage of prior art processes such as those described in U.S. Pat. No. 4,547,324 and U.S. Pat. No. 4,810,426 which use internal alkaline aqueous phase catalysed de-hydrogenation. The reaction with an oxygen-containing gas is an essential feature of the present invention and we have found for example that no reaction takes place if the reaction mixture of the present invention is sparged with nitrogen in place of air or oxygen. It is probable that this different oxidation mechanism accounts for the observed advantages and differences of the present invention as compared with prior art processes such as those described in U.S. Pat. No. 4,547,324 and U.S. Pat. No. 4,810,426 which take place without the involvement of molecular oxygen gas.

The stoichiometric proportion of alkali required to convert N-phosphonomethyl-2-oxazolidinone to its hydrolysis product and subsequently form the alkali salt of the N-phosphonomethylglycine product is 4 moles per mole of N-phosphonomethyl-2-oxazolidinone, including the alkali used to absorb the carbon dioxide liberated during the reaction and form the sodium carbonate. It is preferred to operate the oxidation stage at a pH of from 11 to 13, for example from 11.5 to 12.5. It is preferred therefore to use an amount of alkali sufficient to adjust the pH to the values indicated. Typically there can be used an excess over the stoichiometric value, for example from 5 to 7 moles of alkali per mole of N-phosphonomethyl-2-oxazolidinone. More than 7 moles of alkali per mole of N-phosphonomethyl-2-oxazolidinone may be used if desired, but little advantage is obtained in so doing and decomposition may take place if excessive alkali is present during the oxidation stage. If desired, the total amount of alkali may be added prior to the start of the hydrolysis stage or a proportion of the alkali may be added at the start of the hydrolysis stage and additional alkali added between the hydrolysis and oxidation stages or during the course of the oxidation.

When the oxidation stage is complete, the product is the alkali salt, for example the sodium salt of N-phosphonomethylglycine. If the catalyst is present in the reaction mixture in finely divided form, it is preferred to use a concentration of reactants such that all reactants and the salt of the N-phosphonomethylglycine product remain in solution in order that the catalyst can be recovered for re-use, for example by filtration. In general higher concentrations lead to reduced reaction times, and those skilled in the art will be well able to select optimum concentrations such that the salt of N-phosphonomethylglycine, which is relatively soluble, remains in solution.

Alternatively, if the catalyst is present as a stationary phase through which the reaction medium and oxygen-containing gas are passed, it may be possible to use higher concentrations of reactants such that a proportion of the alkali salt of the N-phosphonomethylglycine product precipitates.

The alkali salt of the N-phosphonomethylglycine product may be used as such or the reaction mixture may be acidified after removal of the catalyst, if present in finely divided form, to precipitate N-phosphonomethylglycine in the form of free acid. After recovery the N-phosphonomethylglycine product may be used as such or may be converted into other well-known salts of N-phosphonomethylglycine which have herbicidal utility.

As illustrated in the Examples hereafter, optimum processes of the present invention may be used to prepare N-phosphonomethylglycine in high conversion and in some instances approaching 100% conversion based on N-phosphonomethyl-2-oxazolidinone fed. The proportions of phosphorous-containing by-products, such as aminomethylphosphonic acid, are generally small and the overall yield of N-phosphonomethylglycine is correspondingly high.

N-Phosphonomethyl-2-oxazolidinone is a known compound readily prepared by the reaction of 2-oxazolidinone, formaldehyde and phosphorous trichloride. 2-Oxazolidinone is also a known compound readily prepared by the reaction of urea and ethanolamine in a solvent such as dimethylacetaminde. During the course of this work we have observed that improved yields may be obtained as compared with the literature process for the manufacture of 2-oxazolidinone if the urea and ethanolamine are both gradually added simultaneously to refluxing solvent.

The invention is illustrated by the following Examples in which all parts and percentages are by weight unless otherwise stated.

PREPARATION 1

2-Oxazolidinone (14.4 g) and paraformaldehyde (4.85 g) were refluxed in acetic acid (125 g) for 2 hours.

After cooling to 65° C., phosphorus trichloride (23.4 g) was added over 10 minutes and the mixture refluxed for a further 2 hours before drowning into 350 mls water and boiling for about 2 hours.

The pH was adjusted to 1.0 and the water removed under vacuum to obtain N-Phosphonomethyl-2-oxazolidinone (28.3 g). Proton nmr on a sample re-crystallised from acetic acid confirmed the structure of this product.

PREPARATION 2

A 250 ml round bottom reaction flask was equipped with a reflux condenser, thermometer and magnetic stirrer bar. dimethylacetamide (52 ml; 48.72 g) was charged and heated to reflux. Ethanolamine (12.20 g) was added from a dropping funnel over 12 minutes at the same time and rate as urea (12.05 g) was added in small portions through a funnel. Upon completion of addition the reaction was left to stir at reflux. The mixture was analyzed by GC at intervals and after 6 hours reaction was judged to be complete. The reaction mass was allowed to cool and then distilled on a water pump to leave a pale yellow oil which solidified on standing. The yield of 2-oxazolidinone as determined by GC was 93.6 %. The proportion of solvent (dimethyl acetamide) was varied from 2.7 to 8.3 mols per mol of ethanolamine without significant adverse effect on the yield.

EXAMPLE 1

Stage 1

A 5 g sample of the material from Preparation 1 was hydrolysed by refluxing for 4 hours in 100 mls of 25% caustic soda solution. Water was removed by applying vacuum to yield a solid mixture containing the sodium salt of phosphonomethylethanolamine and other solid material such as sodium hydroxide and sodium carbonate.

Stage 2

A 1.14 g sample of the product from Stage 1 was dissolved in 50 ml distilled water and the catalyst 5% Pt/C (0.75 g) was added. The pH was measured at 12.2. The mixture was sparged with oxygen at room temperature for 6 hours. Analysis of the resulting solution by P31 n.m.r. and H1 n.m.r. showed that all the starting material had been consumed and that phosphonomethylglycine was the only product.

EXAMPLE 2

A 2.28 g sample of the product of Stage 1 of Example 1 was dissolved in 100 ml of distilled water. This solution at pH 12.2 was divided into two equal parts. To one part was added 0.11 g of additional sodium carbonate. To each part was added of 2.6 g 5% Pt/C catalyst. Each mixture was sparged with oxygen at 55°–60° C. for 6 hours.

Analysis of both solutions by P31 n.m.r. showed complete conversion to phosphonomethylglycine with no other products formed. The addition of sodium carbonate therefore showed no detrimental effect.

EXAMPLE 3

A 3.2 g sample of the product from Stage 1 of Example 1 and containing 1 g phosphonomethyl ethanolamine and 2.2 g of a sodium hydroxide/sodium carbonate mixture was dissolved in 50 mls of distilled water.

A catalyst consisting of 4% Pd/1% Pt/5% Bi on activated carbon (type CEF 196 XRA/W; Degussa) equivalent to 2.3 gms dry weight was added and the mixture diluted to 100 mls with more water.

The mixture was air-blown at 55 mls/min at 55° C. for 1 hour using a turbine agitator running at 1300 rpm.

After removing the catalyst by filtration, P31 nmr showed all of the phosphonomethyl ethanolamine to have been consumed. Traces only of aminomethylphosphonic acid were detected (N-phosphonomethyl glycine to aminomethylphosphonic acid ratio of 98:2) with no other phosphorus compounds having been formed.

EXAMPLES 4 TO 9

The procedure of Example 3 was repeated using a variety of promoted catalysts as shown in the following Table. All catalysts were supported on carbon. The term "Catalyst Loading" used in the Table is defined as the percentage by weight of supported catalyst based on the weight of Product from Stage 1. The results are given in terms of the percentage yield of N-phosphonomethylglycine (PMG). Minor proportions of aminomethanephosphonic acid (AMPA) were formed as by-product. In those Examples in which the combined yield of PMG and AMPA is less than 100% (within experimental error), the residue is unreacted starting material, indicating that the reaction was interrupted prior to completion.

| Example | Catalyst | Catalyst Loading (%) | Oxidation Time (hours) | Yield PMG (%) | Yield AMPA (%) |
| --- | --- | --- | --- | --- | --- |
| 4 | 5% Pd/5% Bi | 40 | 2 | 58 | 16 |
| 5 | 4% Pd/1% Pt/ 5% Bi | 40 | 3 | 90 | 7 |
| 6 | 4% Pd/1% Pt/ 5% Pb | 40 | 2 | 58 | 2 |
| 7 | 4.5% Pd/ 0.5% Pt/5% Bi | 40 | 3 | 89 | 8 |
| 8 | 4% Pd/1% Pt/ 5% Bi | 200 | 1 | 98 | 2 |
| 9 | 4% Pd/1% Pt/ 5% Bi | 10 | 3 | 92 | 8 |

EXAMPLE 10

The procedure of Example 3 was repeated except that the oxidation time was one and a half hours. The yield of PMG was 94%. The catalyst was recovered by filtration and was re-used in a second preparation using the procedure of Example 3. The yield of PMG was 96%. The catalyst was again recovered by filtration and was re-used in a third preparation using the procedure of Example 3. The yield of PMG was 95%.

EXAMPLE 11

This Example illustrates the use of a higher concentration of reactants. A 48 g sample of the product from Stage 1 of Example 1 containing 15 g phosphonomethyl ethanolamine and 33 g of alkali (sodium hydroxide/sodium carbonate) was dissolved in 80 mls of water.

A catalyst consisting of 4% Pd/1% Pt/5% Bi on activated carbon (type CEF 196 XRA/W; Degussa) equivalent to 6 g dry weight was suspended in 20 mls of distilled water.

The catalyst suspension was charged to the oxidiser and air at 55 mls/min was blown through maintaining the temperature at 55° C. the solution of phosphonomethyl ethanolamine was charged to the oxidiser slowly over 3 hours maintaining the temperature at 55° C.

After a further half hour of reaction, the catalyst was removed by filtration and analysis by P31 nmr showed that all the phosphonomethyl ethanolamine had been consumed.

The yield of PMG was estimated to be 92% with about 8% of aminomethylphosphonic acid.

EXAMPLE 12

This Example illustrates the use of acid hydrolysis.

N-Phosphonomethyl-2-oxazolidinone (3 g), water (30 g) and 98% sulphuric acid (10 mg) were charged to a 100 ml Hastelloy pressure vessel fitted with an agitator, pressure gauge and thermocouple.

The vessel was heated to 200° C. over 30 minutes and held at this temperature for 3.5 hours, during which time the pressure was measured at 19 bar. The reaction mixture was cooled to 49° C. and the pressure was released. The contents of the reactor were discharged and analysis (phosphorous nmr) showed the reaction mixture to contain N-phosphonomethylethanolamine. The reaction mixture was adjusted to pH 12.6 by the addition of 47% sodium hydroxide solution and then oxidised using the procedure of Example 3 to give a yield of 96% PMG and 4% AMPA as assessed by quantitative phosphorous nmr.

I claim:

1. A process for the manufacture of N-phosphonomethylglycine and its salts which comprises hydrolysing N-phosphonomethyl-2-oxazolidinone in an aqueous medium and thereafter oxidising the hydrolysis product in an aqueous alkaline medium using an oxygen-containing gas in the presence of an oxidation catalyst at a temperature of from ambient to 100° C.

2. A process for the manufacture of N-phosphonomethylglycine and its salts which comprises hydrolysing N-phosphonomethyl-2-oxazolidinone in an aqueous alkaline medium and thereafter oxidising the hydrolysis product in an aqueous alkaline medium using an oxygen-containing gas in the presence of an oxidation catalyst at a temperature of from ambient to 100° C.

3. A process according to claim 2 wherein the alkali used to provide the alkaline medium for hydrolysis and the alkaline medium for oxidisation is the same and is an alkali metal hydroxide or an alkaline earth hydroxide.

4. A process according to claim 3 wherein the alkali is sodium hydroxide.

5. A process according to claim 2 wherein the hydrolysis takes place at the reflux temperature of the reaction medium under atmospheric pressure.

6. A process according to claim 1 wherein the oxidation catalyst contains a metal selected from the group consisting of platinum, palladium, ruthenium, copper, nickel, zinc and iron.

7. A process according to claim 6 wherein the oxidation catalyst contains in addition, a promoter selected from the group consisting of bismuth, antimony, lead, tin, and selenium.

8. A process according to claim 7 wherein the oxidation catalyst contains a metal selected from the group consisting of platinum or palladium or a mixture thereof in combination with a bismuth promoter.

9. A process according to claim 1 wherein the catalyst is carried on a carbon support.

10. A process according to claim 9 wherein the metal content of the catalyst ranges from 2 to 8% by weight palladium in combination with from 0 to 5% by weight platinum and from 0 to 5% by weight bismuth or wherein the metal content of the catalyst ranges from 2 to 8% by weight platinum in combination with from 0 to 5% by weight palladium and from 0 to 5% by weight bismuth.

11. A process according to claim 1 wherein the oxidation reaction takes place at a pH of from 11 to 13.

12. A process according to claim 1 wherein the catalyst is recovered for re-use.

\* \* \* \* \*

UNITED STATES PATENT AND TRADEMARK OFFICE
CERTIFICATE OF CORRECTION

PATENT NO.    : 5,500,485
DATED         : March 19, 1996
INVENTOR(S)   : Ian Hodgkinson It is certified that error appears in the above-identified patent and that said Letters Patent is hereby corrected as shown below:

On title page insert:

[73] Assignee: Zeneca Limited, London, England

Signed and Sealed this

Twenty-fourth Day of September, 1996

Attest:

BRUCE LEHMAN

*Attesting Officer*   *Commissioner of Patents and Trademarks*